United States Patent [19]

Diehl et al.

[11] Patent Number: 5,451,494
[45] Date of Patent: Sep. 19, 1995

[54] PHOTOGRAPHIC ELEMENTS CONTAINING ACYL SUBSTITUTED OXONOL DYES

[75] Inventors: Donald R. Diehl; Margaret J. Helber, both of Rochester; Pamela M. Ferguson, Farmington; Anne E. Edwards, Rochester; Nona V. Spitzner, Bergen, all of N.Y.

[73] Assignee: Eastman Kodak Company, Rochester, N.Y.

[21] Appl. No.: 279,574

[22] Filed: Jul. 22, 1994

Related U.S. Application Data

[63] Continuation-in-part of Ser. No. 235,036, Apr. 28, 1994, abandoned.

[51] Int. Cl.⁶ .................. G03C 1/835; G03C 1/19; G03C 1/18; G03C 1/20
[52] U.S. Cl. .................... 430/522; 430/517; 430/570; 430/578; 430/593; 430/595; 544/296
[58] Field of Search ............... 430/510, 517, 592, 593, 430/595, 578, 570, 522; 544/296

[56] References Cited

U.S. PATENT DOCUMENTS

| | | | |
|---|---|---|---|
| 2,415,927 | 2/1947 | Anish | 430/578 |
| 3,247,127 | 4/1966 | Bailey | 252/300 |
| 3,370,950 | 2/1968 | Lodewijk et al. | 96/83 |
| 3,653,905 | 4/1972 | Depoorter et al. | 96/84 |
| 4,042,397 | 8/1977 | Moelants et al. | 96/84 |
| 4,078,933 | 3/1978 | Sugiyama et al. | 96/84 |
| 4,179,294 | 12/1979 | Sugiyama et al. | 430/522 |
| 4,945,033 | 7/1990 | Deguchi et al. | 430/522 |
| 5,013,636 | 5/1991 | Ohno et al. | 430/522 |
| 5,035,977 | 7/1991 | DeBoer et al. | 430/200 |
| 5,035,986 | 7/1991 | Sakai et al. | 430/522 |
| 5,213,956 | 5/1993 | Diehl et al. | 430/522 |
| 5,260,179 | 11/1993 | Diehl et al. | 430/522 |

FOREIGN PATENT DOCUMENTS

| | | |
|---|---|---|
| 1090442 | 4/1989 | Japan . |
| 1205158 | 8/1989 | Japan . |

*Primary Examiner*—Richard L. Schilling
*Attorney, Agent, or Firm*—Gordon M. Stewart

[57] ABSTRACT

A photographic element containing a dye of the structure (I) as a filter dye:

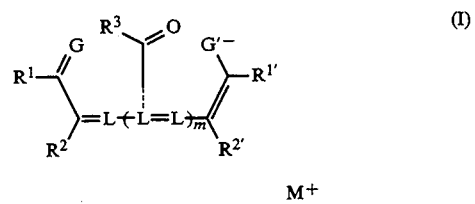

wherein:

G is oxygen, substituted nitrogen, or $C(CN)_2$;

$R^1$, $R^{1'}$, $R^2$, $R^{2'}$ independently represent H or a substituent, or $R^1$ and $R^2$, $R^{1'}$ and $R^{2'}$ may form a ring;

$R^3$ is an alky, aryl, alkyloxy, aryloxy, amino, or heterocyclic, any of which may be substituted or unsubstituted;

m is 0, 1, 2 or 3;

all of the L together define a methine chain, each L representing a methine any of which may be substituted or unsubstituted; and $M^+$ is a cation.

25 Claims, No Drawings

PHOTOGRAPHIC ELEMENTS CONTAINING ACYL SUBSTITUTED OXONOL DYES

CROSS-REFERENCE TO RELATED APPLICATIONS

This is a Continuation-In-Part of application Ser. No. 235,036, filed Apr. 28, 1994, now abandoned.

FIELD OF THE INVENTION

This invention relates to dyes and, more particularly, to novel oxonol type dyes that are useful in photographic materials.

BACKGROUND OF THE INVENTION

A wide variety of dyes is employed in photographic materials. In addition to diverse dyes used to form images in color photographic elements, spectral sensitizing dyes are used to extend the sensitivity of silver halides, which are inherantly sensitive only to blue light, to other wavelengths of radiation. Among the dyes commonly employed for this purpose are the cyanines and merocyanines, which are discussed in T. H. James, editor, *The Theory of the Photographic Process*, 4th Edition, Macmillan, New York, 1977, Chapter 8, and in F. M. Hamer, *Cyanine Dyes and Related Compounds*, Wiley, New York, 1964.

Dyes are also used in color photographic materials as filters, typically located in overcoats, interlayers or undercoats, to absorb incident radiation and improve image sharpness. Intergrain absorber dyes may also be added directly to a spectrally sensitized silver halide emulsion to absorb light and thereby modify the sensitivity of the emulsion. In addition to the previously mentioned cyanine and merocyanines, various oxonol and arylidene dyes are frequently utilized for these purposes. A discussion of arylidene dyes can be found in K. Venkataraman, *The Chemistry of Synthetic Dyes*, Academic Press, New York, 1970, Volume III.

Historically, the oxonol class of dyes have been particularly useful in photographic systems for light filtration only. For that reason, a very large number of oxonol dye structural modifications have been described in the patent literature. For example a wide variety of ketomethylenes, or acidic methylene groups, may compose the end groups of the chromophore. Such groups may be carbocyclic, heterocyclic, or a fused ring system. Such ring systems are well known in the literature and are sometimes referred to as ketomethylenes. For example, those listed in Hamer, *Cyanine Dyes and Related Compounds*, pages 469–494 and 595–604, which include the ketomethylene groups benzoylacetonitrile, 2-pyrazolin-5-one, pyrazolindione, chromandione, cyclohexanedione, dioxanedione, furanone, isoxazolinone, and pyrandione among others.

In addition, hydroxypyridone oxonol dyes have been described in GB 1,278,621, and pyrazolopyridine oxonol dyes have been described in EP-A-0 295 698. The search for new bathochromic dyes has led to some novel oxonol dye dye structures. For example, tricyanopropene dyes are described in U.S. Pat. No. 5,213,956, while novel imines dyes are described in U.S. Pat. No. 5,260,179.

Oxonol dyes may typically be monomethine, trimethine, pentamethine, or heptamethine oxonol dyes. The methine (CH) units are often unsubstituted although some substituted methine (L=CR) units have also been described. For example, Hall, Burrows, and Kirk report in European Patent Application 397,435 that when G in the formula therein represents an oxygen atom and m is equal to 3 some of the groups $L^1$ to $L^3$ represent the elements of a 5, 6, or 7 membered carbocyclic, heterocyclic or fused ring system. U.S. Pat. No. 4,042,397 and U.S. Pat. No. 3,653,905 describe dyes with a substituted barbituric acid group in which the methines may be unsbustituted or substituted with, for example, alkyl, aralkyl, aryl or carboxyl. U.S. Pat. No. 5,035,977 describes oxonol type dyes with any of a large variety of possible methine substituents.

Given the usefulness of oxonol type dyes, it would be desirable to provide new classes of oxonol dyes which exhibit good characteristics as a filter dye in photographic elements and which may be readily prepared.

SUMMARY OF THE INVENTION

The present invention therefore provides a novel class of oxonol dyes which has particular acyl substituents in the middle of a methine chain, as well as photographic elements containing such novel dyes as a filter dye. These dyes are readily prepared from available starting materials, have good light absorbance properties, do not act to de-sensitize a sensitized silver halide, and are readily removed from conventional wet processed silver halide photographic materials by being washed out and decolorized by components in the processing solutions. Thus, the dyes of the present invention leave little or no post-processing retained dye stain in photographic materials and are environmentally advantageous in being decolorized and destroyed.

In particular, the present invention provides dyes of the structure (I) as a filter dye, and provides a photographic element containing such novel dyes:

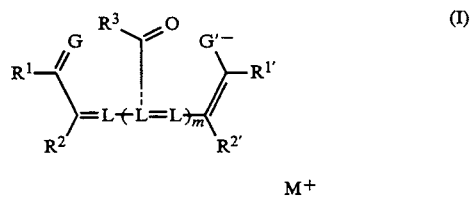

wherein:
- G is oxygen, substituted nitrogen, or —C(CN)$_2$;
- $R^1$, $R^{1'}$, $R^2$, $R^{2'}$ independently represent H or a substituent, or $R^1$, $R^2$, $R^{1'}$, and $R^{2'}$ may form a ring;
- $R^3$ is an alkyl, aryl, alkyloxy, aryloxy, amino, or heterocycle, any of which may be substituted or unsubstituted;
- m is 0, 1, 2 or 3;
- all of the L together define a methine chain, each L representing a methine any of which may be substituted or unsubstituted; and
- M$^+$ is a cation, such as H$^+$, Et$_3$NH$^+$, C$_5$H$_5$NH$^+$, Na$^+$, K$^+$, and the like.

Methods of synthesizing particular dyes of formula (I) are also provided.

Embodiments of the Invention

It should be noted that dyes of formula (I) (or of formula Ia to Ie) described herein, need not be symmetric in structure about the methine chain. That is, G and G' need not be the same Also $R^1$ and $R^{1'}$ or $R^2$ and $R^{2'}$ need not be the same. However, typically the dyes of the present invention will be symmetric (that is, G=G', $R^1=R^{1'}$, and $R^2=R^{2'}$) Further, preferably $R^3C(O)$— shown is substituted on the L at the middle of the methine chain.

In the above formula (I), $R^2$ and $R^{2'}$ may particularly represent a moiety in conjugation with $G^-$ and $G'^-$, respectively. In this regard $G^-$ is referred to since it can be considered as present in one of the resonance structures of (I). Particularly, $R^2$ and $R^{2'}$ may each contain an atom with an available electron pair positioned in conjugation with $G^-$ or $G'^{31}$, which atom may for example be an O, N, Se or S, or is a C with at least one electron withdrawing group bonded thereto, or $R^2$ or $R^{2'}$ may be a group containing a benzene ring. Reference to a particular "group" herein, it will be understood to include both substituted and unsubstituted forms of the referenced group. By being positioned in "conjugation" with $G^-$ or $G'^-$, is meant that there is a conjugated system between the $G^-$(or $G'^-$) and $R^2$(or $R^{2'}$). Such systems are generally known in organic chemistry and refer to a chain in which a single bond, and a double or triple bond, appear alternately. As to electron withdrawing substituents, these are discussed in March, *Advanced Organic Chemistry*, 3rd Ed., J. March, (John Wiley Sons, New York; 1985) at pages 20–21, 228–229, 386–387, 494–497. In particular, preferred electron withdrawing substituents in each case described herein, would have a Hammett $\sigma_p$ constant of greater than 0.1 (or greater than 0.3) and preferably between 0.1 to 1.0 (for example, between any of 0.3, 0.4, 0.5 or 0.6 to 1.0). Hammett $\sigma_p$ values are discussed in the foregoing *Advanced Organic Chemistry*. Note that the "p" subscript refers to the fact that the $\sigma$ values are measured with the substituents in the para position of a benzene ring. Additional tables relating to Hammett $\sigma_p$ constants can be found in *Chemical Reviews* Volume 91, pages 165–195 (authored by C Hansch et al.).

$R^1$ and $R^{1'}$ may particularly include any of the alkyl, alkoxy, aryl, aryloxy, or acyl groups. $R^1$ or $R^{1'}$ may also be electron withdrawing groups as already defined.

In particular, $R^1$ and $R^2$, and $R^{1'}$ and $R^{2'}$, together with the carbon atoms to which they are attached and G or G', may independently represent a benzoylacetonitrile, 2-pyrazolin-5-one, pyrazolindione, chromandione, cyclohexanedione, dioxanedione, furanone, isoxazolinone, pyrandione hydroxypyridone, pyrazolopyridine, tricyanopropene or barbituric acid. Any one of the foregoing may be substituted or unsubstituted.

As to $R^3$, when this is an amino it may be unsubstituted or substituted with an alkyl group or aryl group.

One class of dyes of formula (I) include those of formula (Ia) below:

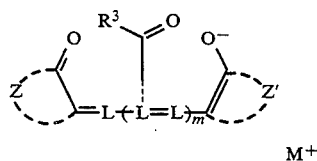

wherein:
Z and Z' are atoms which, together with the C—CO to which they are attached, independently define a 2-pyrazolin-5-one, pyrazolindione or barbituric acid, any of which may be substituted or unsubstituted.

Other specific types of dyes of formula (I) include those of formulae (Ib), (Ic), (Id) or (Ie) below:

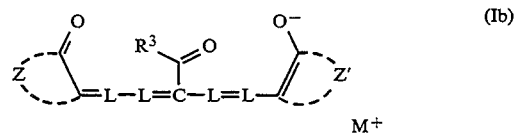

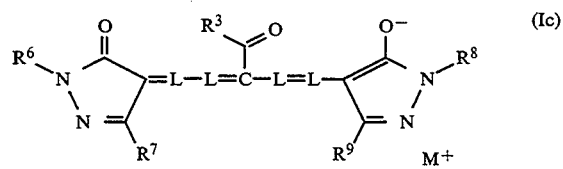

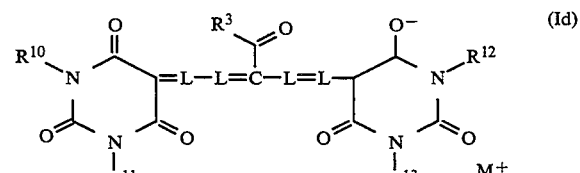

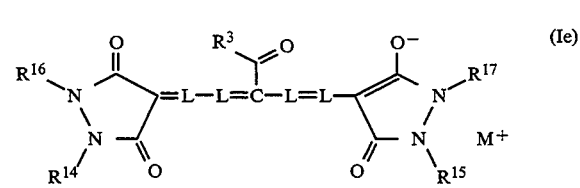

wherein:
R7 and R9 are independently H, or alkyl, alkoxy, aryl, aryloxy, acyl, amino, cyano, carbonamido, or carbamoyl, any of which may be substituted or unsubstituted; and R6, R8, R10, R11, R12, R13, R14, R15, R16 and R17 are independently H, alkyl or aryl, any of which may be substituted or unsubstituted.

In the above formulae, acyl for $R^7$ and $R^9$ includes aldehyde, carboxyl, alkylcarbonyl, arylcarbonyl, aryloxycarbonyl or alkoxycarbonyl.

Any of the substituted or unsubstituted alkyl or alkoxy described herein for any of the substituents (particularly any of the R substituents) may include a substituted or unsubstituted alkyl (including cycloalkyl) or alkoxy of 1 to 20 (preferably 1 to 8) carbon atoms. Examples of unsubstituted alkyl groups are methyl, ethyl, propyl, isopropyl, butyl, isobutyl, t-butyl, pentyl, hexyl, octyl, 2-ethylhexyl, and the like. Cycloalkyl groups may particularly be of 5 to 14 carbon atoms, and can include cyclopentyl, cyclohexyl, 4-methylcyclohexyl, and the like. Any alkenyl substituents can be 2 to 20 (preferably 2 to 8) carbon atoms. Examples of alkenyl groups can be vinyl, 1-propenyl, 1-butenyl, 2-butenyl, and the like. Any of the aryl or aryloxy groups can particularly have from 6 to 14 carbon atoms. Aryl may include phenyl, naphthyl, styryl, and the like, while aryloxy groups may include the oxy derivatives of the foregoing aryl groups. Useful heterocyclic groups may particularly be of 5 to 14 carbon atoms and can include substituted or unsubstituted thiazole, selenazole, oxazole, imidazole, indole, benzothiazole, benzindole, naphthothiazole, naphthoxazole, benzimidazole, pyridine, pyrazole, pyrrole, furan, thiophene, and the like. Substituents on any of the foregoing alkyl, alkenyl, aryl, heterocyclic or other groups can include, for example, aryl. Thus, a substituted alkyl includes aralkyl such as benzyl, phenethyl, and the like. While the methines, L, other than that substituted with the described acyl group, may be unsubstituted, any of them may optionally be substituted with groups such as an alkyl group (including sulfoethyl), alkoxy group, aryloxy group, aryl group, carboxy group, halogen, cyano, and the like. Substituted methines include the possibility that any of the methines together with a suitable number of other atoms, may form a carbocyclic (particularyl cycloalkyl) or heterocyclic ring, particularly a substituted or unsubstituted cyclopentyl or cyclohexyl ring. For example, a cyclohexyl group may be formed from the middle methine carrying the acyl group, together with the carbon on either side thereof plus three additional carbon atoms.

Useful substituents for any of the alkyl, alkenyl, aryl, heterocyclic, or other groups described above include halogen (such as chloro or fluoro), alkoxy (particularly of from 1 to 6 carbon atoms), acyl, alkoxycarbonyl, aminocarbonyl, carbonamido, carboxy, sulfamoyl, sulfonamido, sulfo, nitro, hydroxy, amino, cyano and the like.

Optionally, any of the above described dyes of formula I (and more particularly, formulae Ia to Ie) may exclude those dyes having a barbituric acid ring with a ring nitrogen substituted by a phenyl or a barbituric acid ring with a ring nitrogen substituted by an alkylene group. Alternatively, dyes of the present invention may exclude any of those dyes carrying a barbituric acid group.

As to the method of preparing particular dyes of a type of formula (I), this method specifically provides for the preparation of symmetric dyes of formula (If) below as shown by the following reaction sequence:

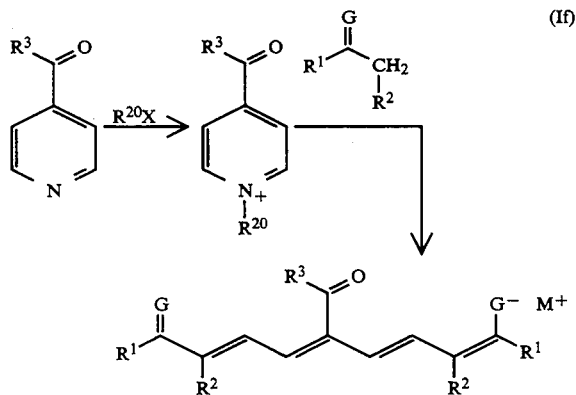

In the above method, R3 preferably represents methyl, phenyl, ethoxy, methoxy, or amino, any of which may be substituted or unsubstituted (particularly with substituents as already defined above); $R^{20}X$ represents 1-chloro-2,4-dinitrobenzene, and $R^1$, $R^2$, and G represent the elements necessary to form a substituted or unsubstituted acidic methylene moiety (alternately referred to as "active methylene" moiety). Acidic (or "active") methylene moieties can be represented by:

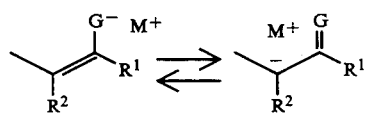

Such moieties, where G represents O, are well known in the art and are described, for example, in the previously mentioned Hamer, *Cyanine Dyes and Related Compounds*, pages 469–494 and 595–604. In accordance with the present invention, preferred acidic methylene moieties include those derived from benzoylacetonitrile, 2-pyrazolin-5-one, pyrazolidindione, barbituric acid, rhodanine, indandione, benzofuranone, chromandione, cyclohexanedione, dioxanedione, furanone, isoxazolinone, pyrazolopyridine, pyridone, isoxazolidinedione, pyrandione, and tricyanopropene ($R^2=CN$, $G=C(CN)_2$). Further details of preferable groups defined by $R^1$, $R^2$ and G (including those defined in formulae Ic, Id and Ie) have already been discussed above. In a preferred embodiment of the method, $R^3$ represents methyl, phenyl, ethoxy, methoxy, or substituted or unsubstituted amino (possible substituents for which, are discussed above). $R^{20}$ may represent 2,4-dinitrophenyl or cyano. X may represent a halogen such as chloro or bromo. In a particularly preferred embodiment, $R^4X$ represents 1-chloro-2,4-dinitrobenzene.

Dyes of formula I may have at least one (or two, three or more) acid or acid salt group present to aid in their removal from the photographic element during processing. For example, the dye may have at least one, two, three or more groups selected from carboxy, sulfonamido, sulfamoyl, sulfato or sulfo.

Photographic elements of the present invention may contain dyes of formula (I) for a wide variety of purposes. One example is where the dye is in the form of a solid particle filter dye dispersion, in a manner similar to that as previously disclosed in patents U.S. Pat. No. 4,803,150; 4,855,221; 4,857,446; 4,900,653; 4,900,654; and 5,098,820. Solid particle dispersions of compounds of formula (I) may be present in the photographic element as general purpose filter dyes, alone or in combination with other filter dyes. In such an application the particles of the dye might have an average particle size of 0.01 μm to 100 μm, preferably 0.1 μm to 10 μm, and more preferably 0.1 μm to 2 μm. Dyes of the formula (I) incorporated into solid particle dispersions require the presence of at least one base-ionizable functionality including, but not restricted to, carboxy (—COOH), sulfonamido (—NHSO$_2$R$^{22}$) or sulfamoyl (—SO$_2$NHR$^{23}$) where $R^{22}$ and $R^{23}$ represent alkyl or alkylthio groups (the alkyl of which, in either case may particularly have the number of carbon atoms and substituents as defined above for alkyl groups). In addition, $R^{22}$ can be hydrogen.

Pentamethine dyes (that is, in which m=2) of formula (I) absorb strongly in the wavelength region of 550 to 800 nm. Such dyes would find particular use as long green, red, and near infrared (NIR) filter, antihalation, or sharpness enhancing dyes in photographic systems.

Dyes of formula I which are present as solid particle dispersions as described above should not be substituted with strongly acidic groups such as sulfo, (SO$_3^{31}$ ), which would tend to increase the solubility of the dye sufficiently to cause dissolution of the dye at pH's employed during coating of the photographic element. As a result, solid particle filter dye dispersions of dyes of formula (I) will be insoluble at coating pH's of 6 or less (generally 4 to 6) and soluble at processing pH's of 8 or more (generally 8 to 12). Thus, they do not interact with other components of the photographic elements during coating or storage but are fully solubilized during photographic processing.

Water soluble filter dyes of the formula (I) can also be present either within a silver halide emulsion layer of the element as an intergrain absorber or immobilized by cationic mordants in a separate layer, or coated in a layer on the support on the side opposite to the layers containing silver halide emulsions. Dyes of formula (I) used in this manner would incorporate one or more solubilizing groups such as sulfo ($-SO_3^-$) or sulfato ($-OSO_3^-$). Such dyes would readily wash out of the silver halide emulsions upon normal photographic processing.

Amounts of dyes described which can be used in photographic elements of the present invention can vary widely. Particularly the amount used in such elements is from 0.1 mg/m$^2$ to 1000 mg/m$^2$, or preferably from 1 mg/m$^2$ to 100 mg/m$^2$.

Dyes of formula (I) which are not removed from photographic elements can also function, particularly in color negative materials, as printer compatibility dyes to add $D_{min}$ at desired wavelenghts. Dyes of the present invention can also be used as a tint in photographic element supports.

More generally, dyes of the formula (I) may be in a hydrophilic layer of a photographic element which is either a radiation sensitive layer or a non-radiation sensitive layer. Further, the dyes may be located on the same side of a support of a photographic element as a radiation sensitive layer, or on the opposite side of the support. More specifically, the dyes (either particle or water soluble) would be incorporated in an anti-halation layer or an anti-halation subbing layer.

The following are examples of dyes of formula (I):

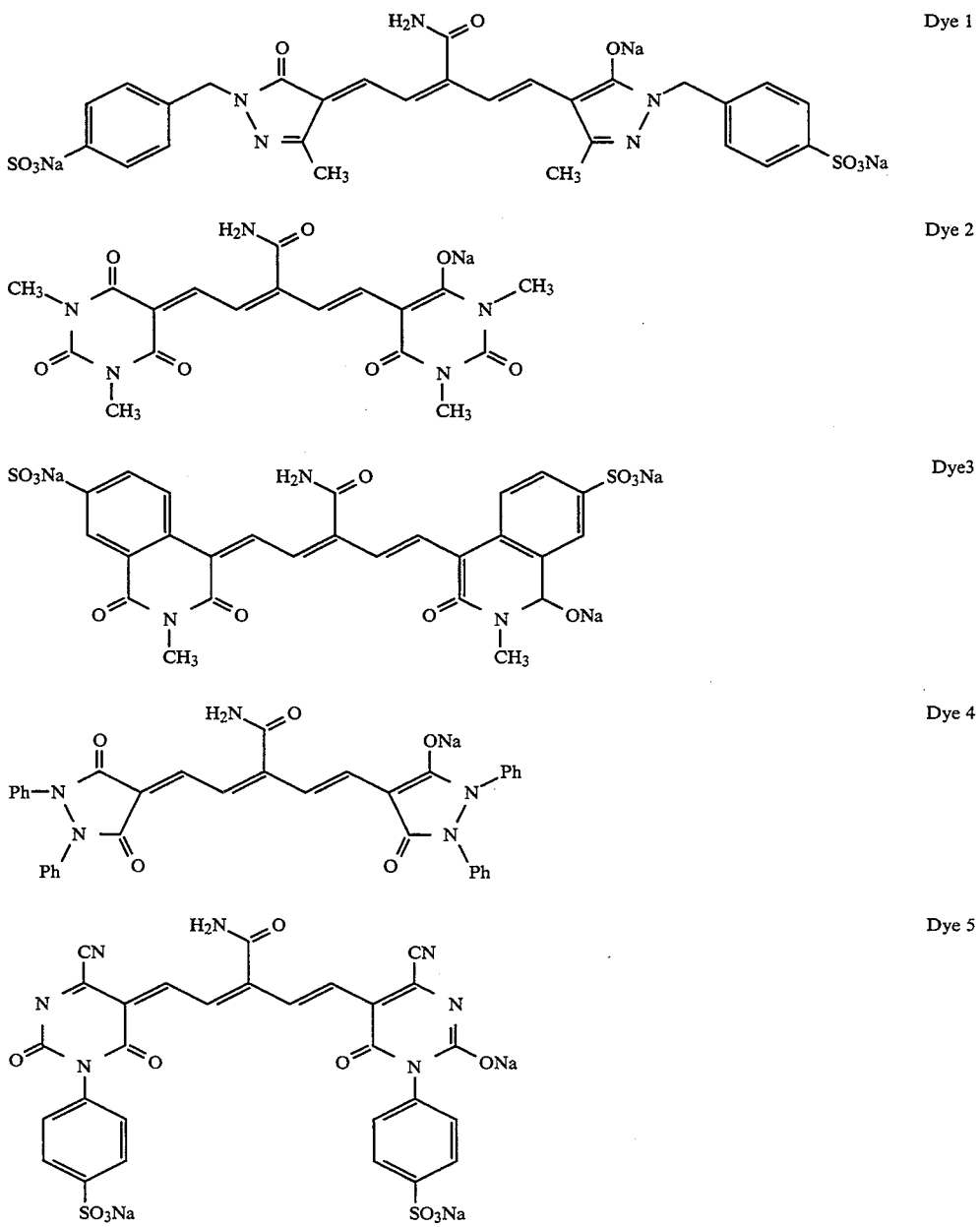

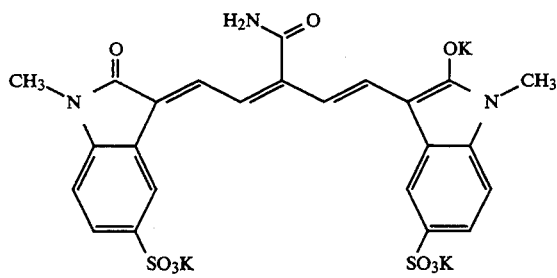
Dye 6
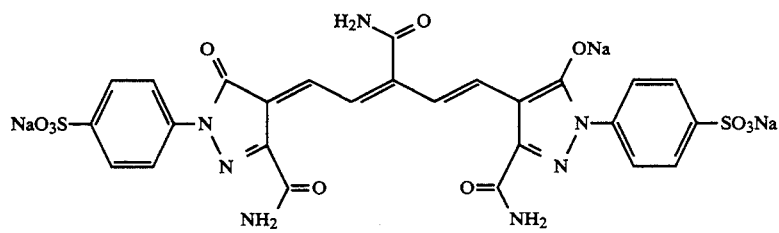
Dye 7
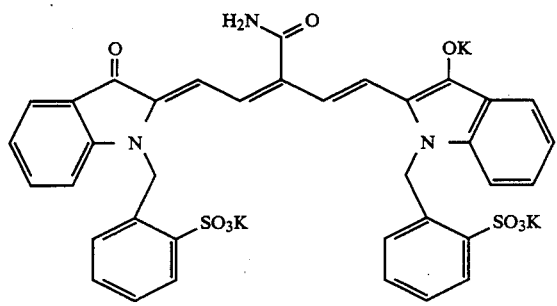
Dye 8
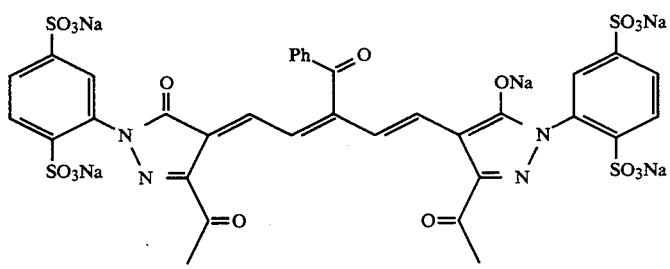
Dye 9
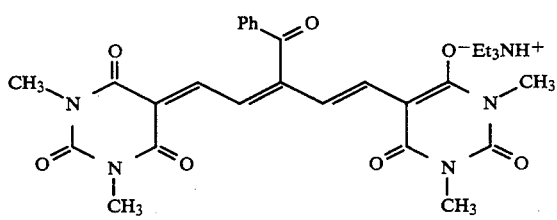
Dye 10
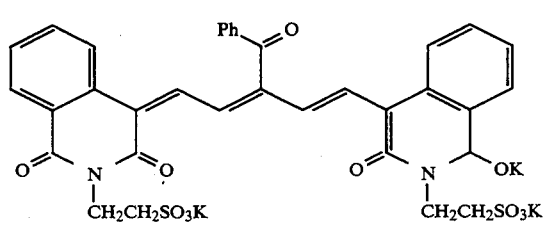
Dye 11

-continued
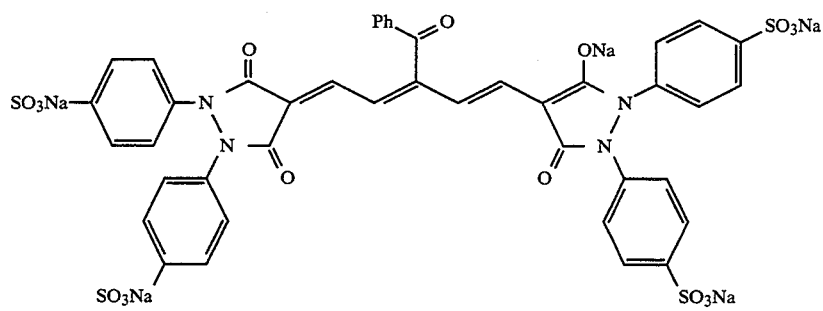
Dye 12
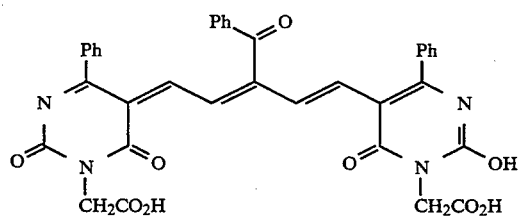
Dye 13
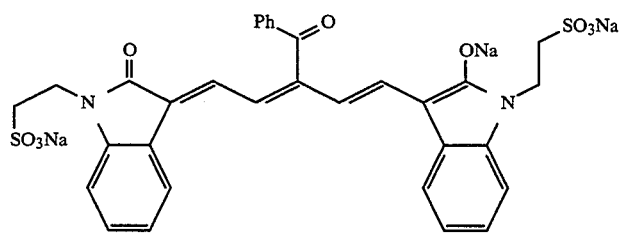
Dye 14
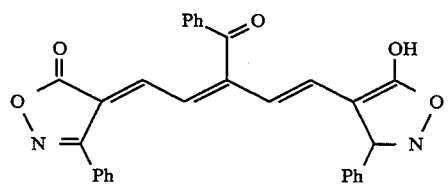
Dye 15
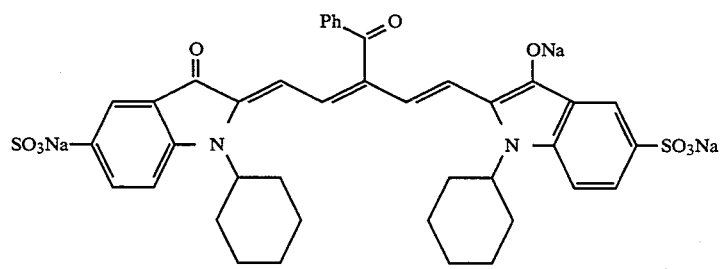
Dye 16
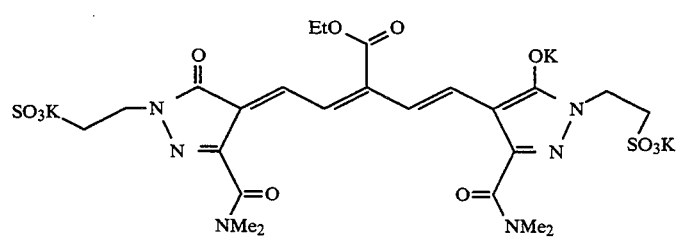
Dye 17
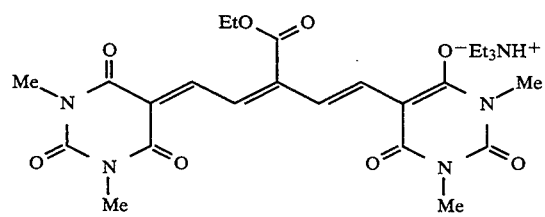
Dye 18

-continued
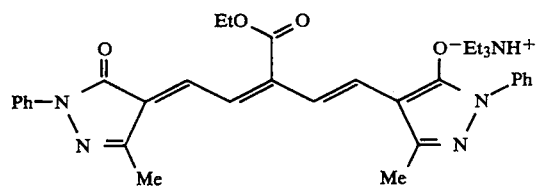
Dye 19
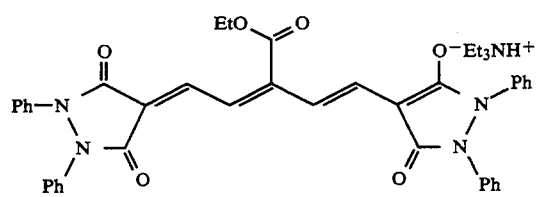
Dye 20
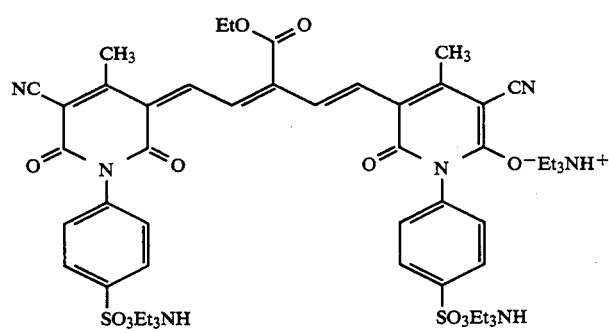
Dye 21
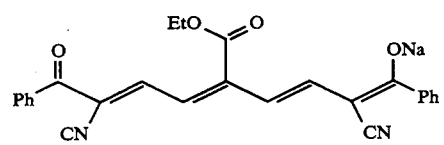
Dye 22
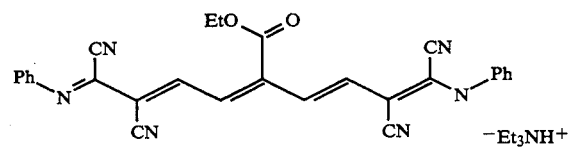
Dye 23
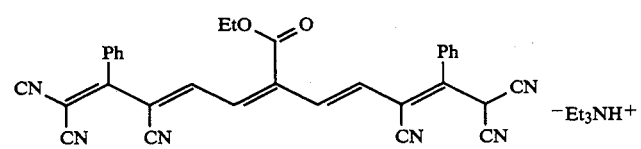
Dye 24
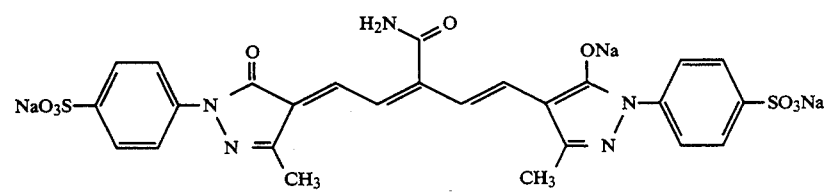
Dye 25
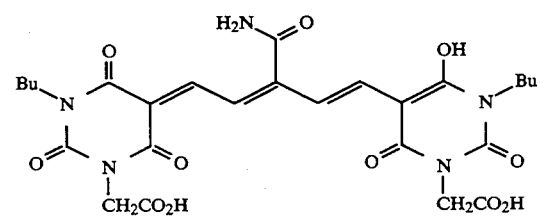
Dye 26

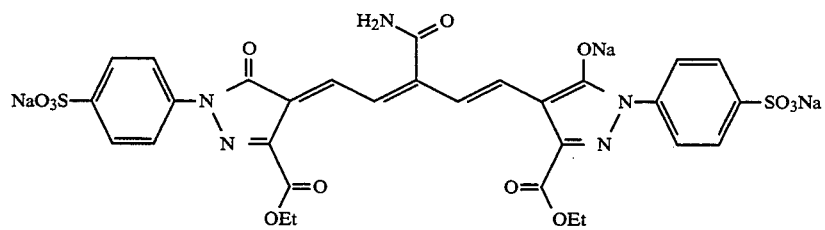
Dye 27
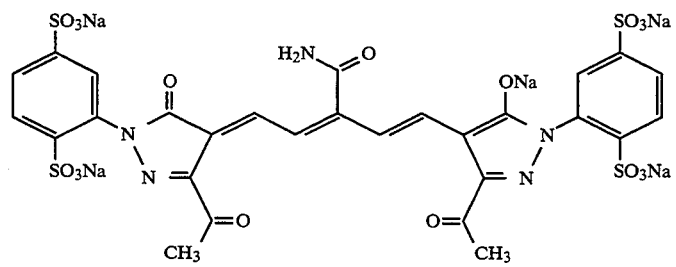
Dye 28
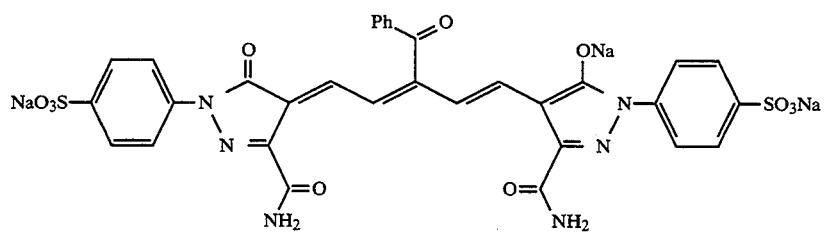
Dye 29
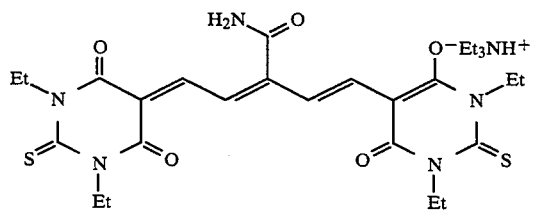
Dye 30
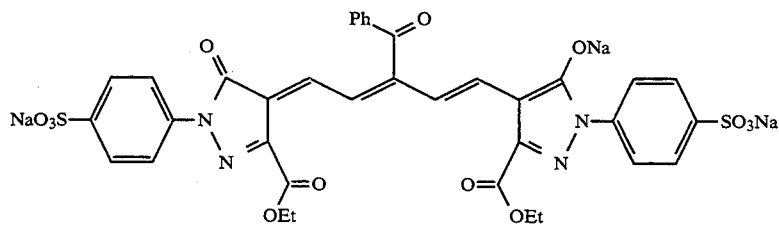
Dye 31
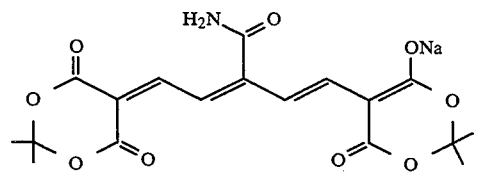
Dye 32
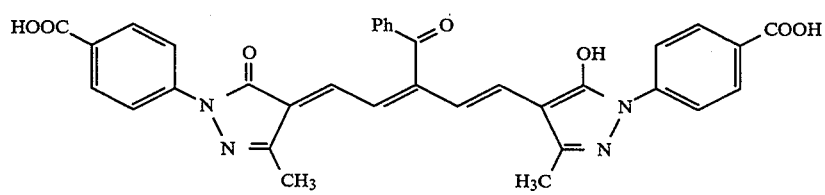
Dye 33

-continued
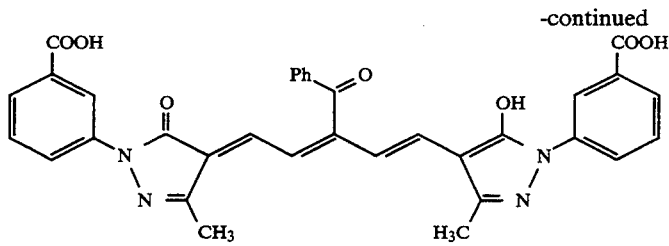
Dye 34
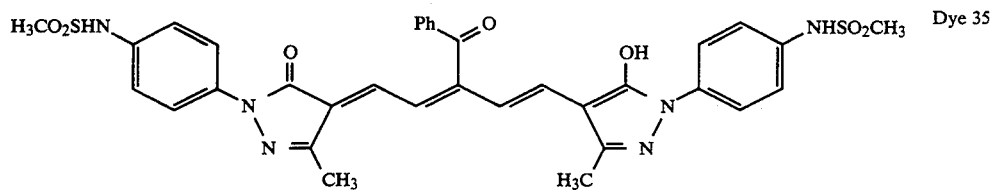
Dye 35
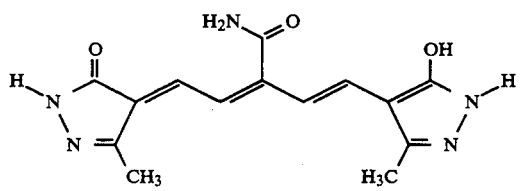
Dye 36
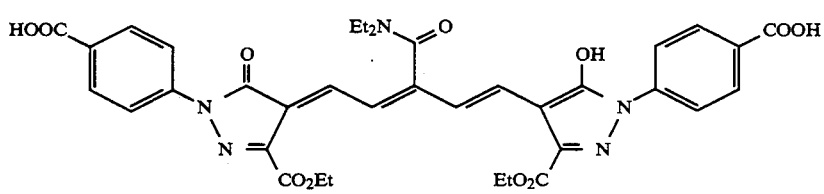
Dye 37
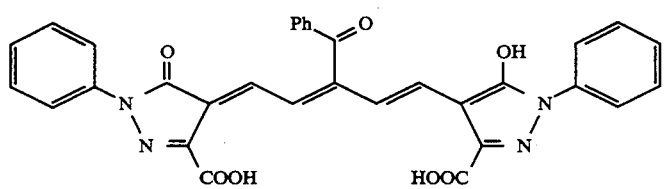
Dye 38
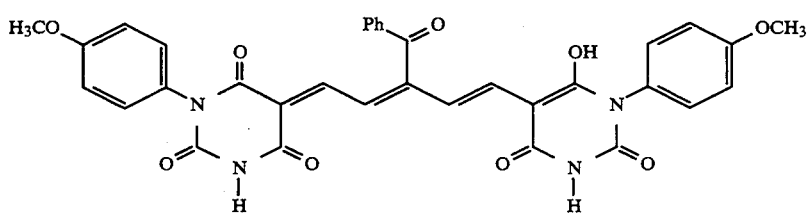
Dye 39
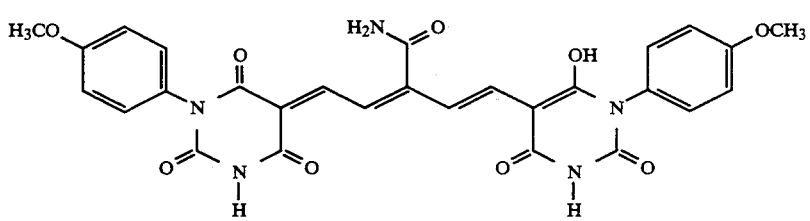
Dye 40
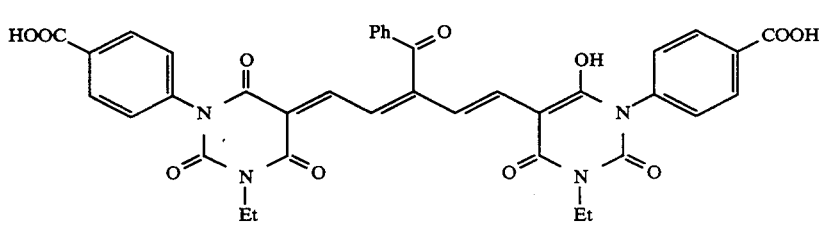
Dye 41

-continued
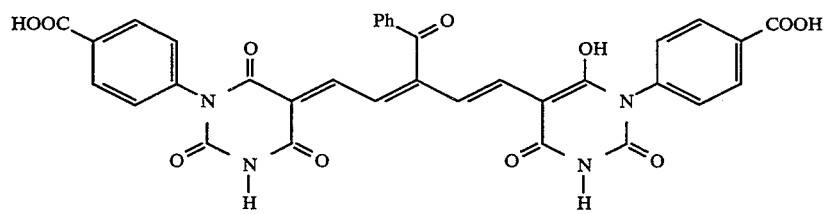
Dye 42
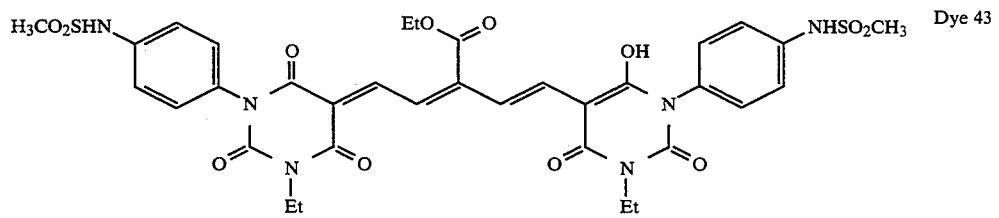
Dye 43
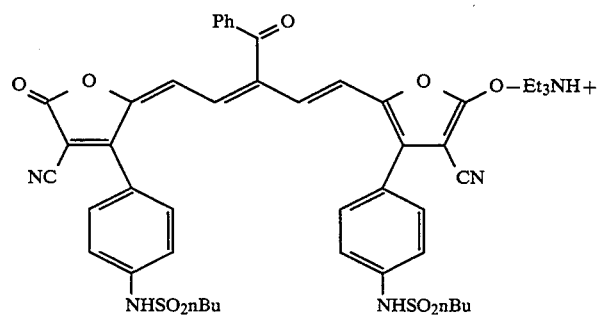
Dye 44
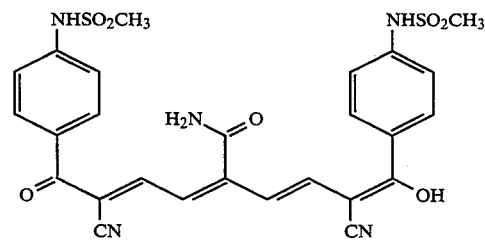
Dye 45
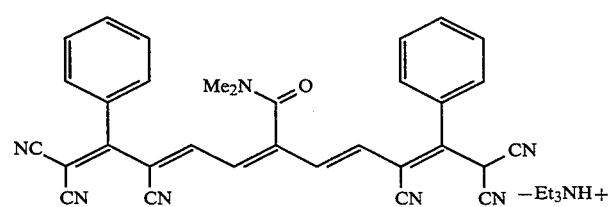
Dye 46
Dye 47

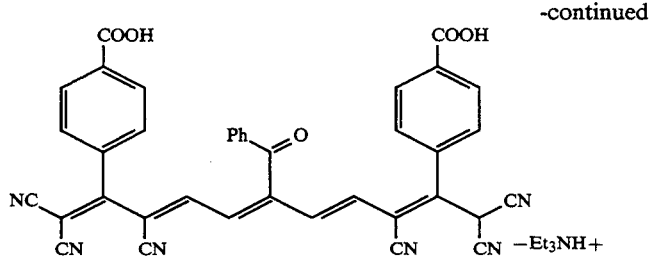
Dye 48
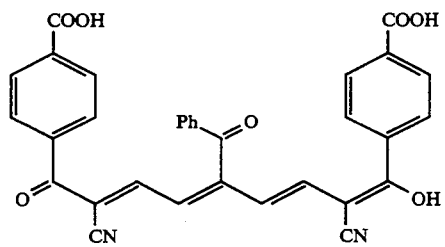
Dye 49
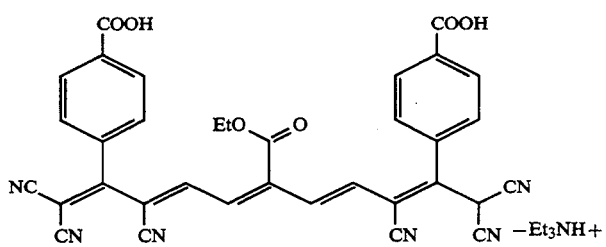
Dye 50
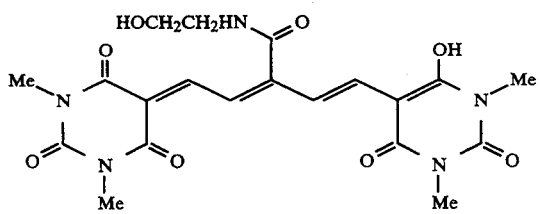
Dye 51
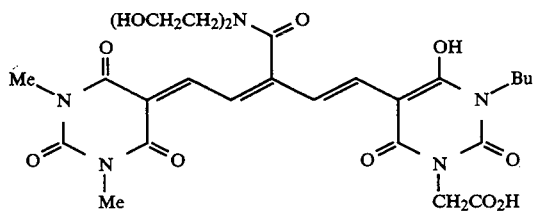
Dye 52
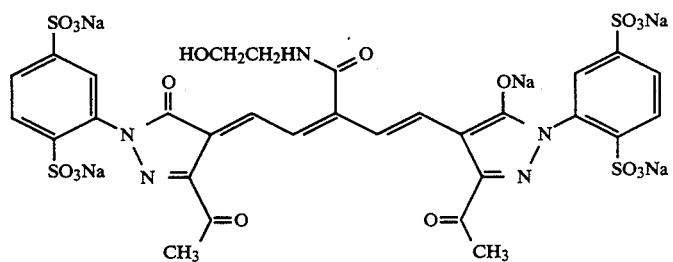
Dye 53
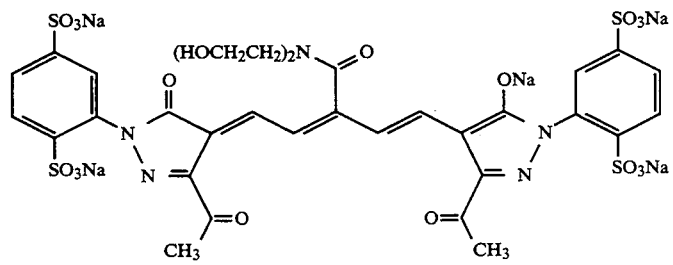
Dye 54

-continued
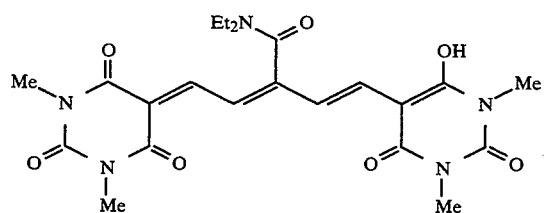
Dye 55
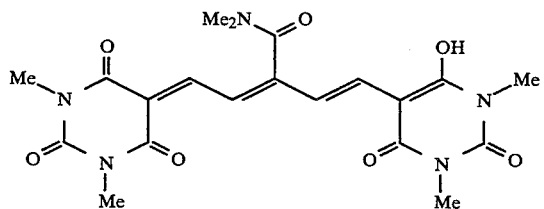
Dye 56
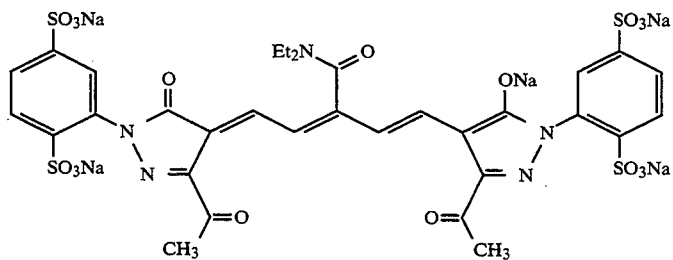
Dye 57
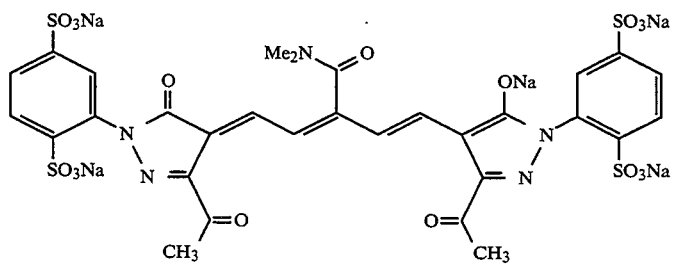
Dye 58
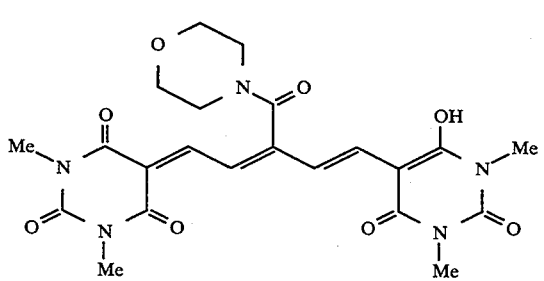
Dye 59
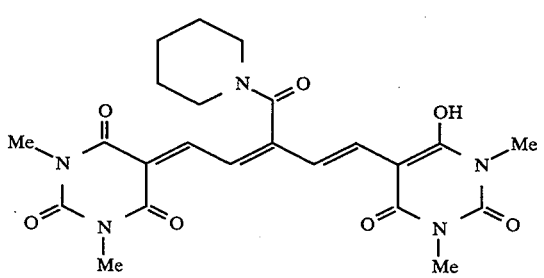
Dye 60

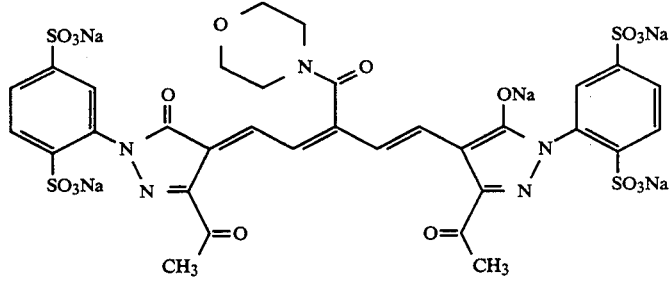
Dye 61
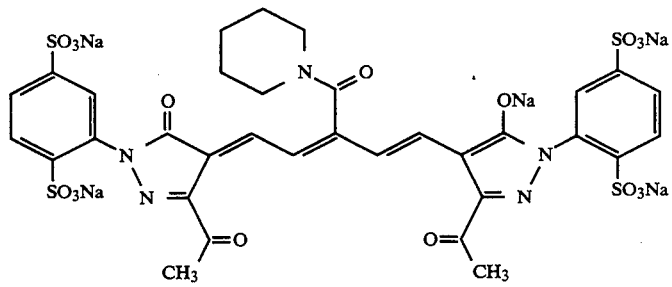
Dye 62
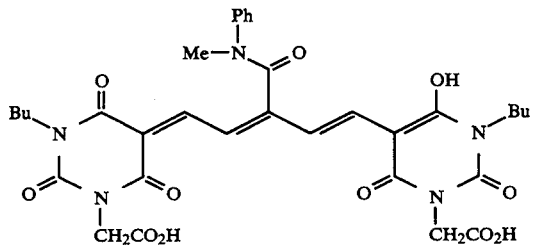
Dye 63
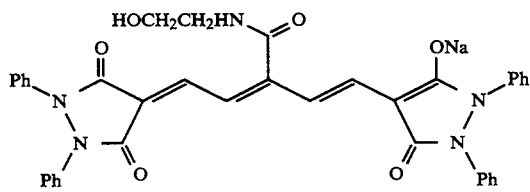
Dye 64
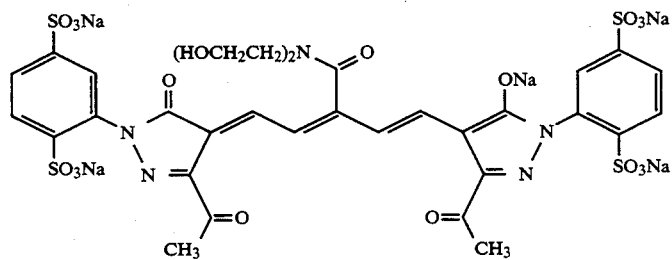
Dye 65
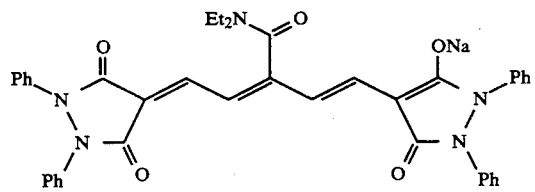
Dye 66
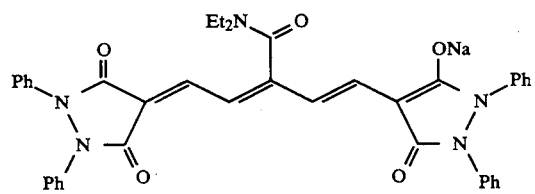
Dye 67

-continued

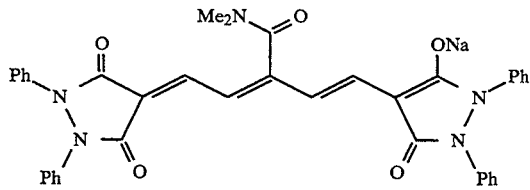

Dye 68

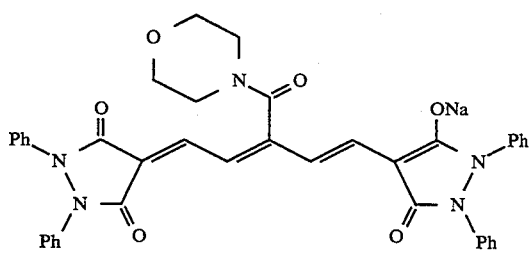

Dye 69

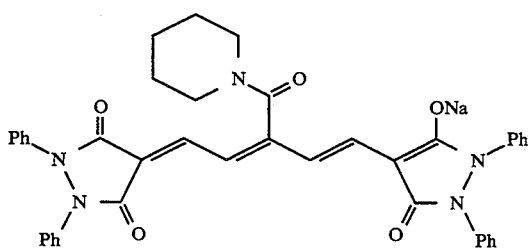

Dye 70

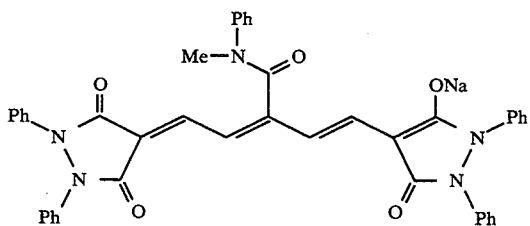

Dye 71

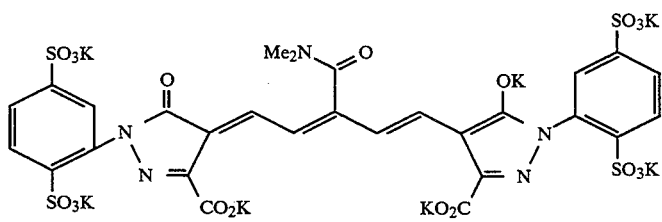

Dye 72

Dyes of type II, III, IV and V (which are all dyes of formula (I)), where $R_3$, $R_{10}$ and $R_{11}$ are the same as described above, and $R_{24}$ is alkyl (which may be substituted or unsubstituted), may be prepared by methods shown below, for example using barbituric acids as an active methylene compound. Other active methylene compounds, like pyrazolone and the like, would be expected to produce other chain acyl oxonol dyes in a similar manner. The required trialkoxy compounds (A) are known in the literature: R. G. Jones, J.A.C.S., 1951, 73, 5168–5169, and W. Kantlelehner, J. Kapassakalidis, and T. Maier, Liebigs Ann. Chem. 1980, 1448–1454. Preparation of the required trimethoxypropene (C) may be accomplished by routine acetal formation from known diformyl compounds, for example methyl diformyl acetate, (D) where $R_3$ is methoxy, whose synthesis is described in Organic Syntheses Col. Vol. 7, 323–325, ed. J. P. Freeman, John Wiley and Sons, Inc., New York, 1990. Methods for the preparation of bridged pentamethine or heptamethine dianil compounds are described in the literature, for example: Y. L. Slominski and L. M. Shulezhko, Ukr. Khim. Zh., 1974, 40, 625–629; Y. L Slominski, I. D. Radchenko and A. I. Tolmachev, Ukr. Khim. Zh., 1975, 41, 760–762; S. M. Makin, T. N. Boiko, and A. I. Pomagaev, Zh. Organ. Khim., 1988, 24, 410–415; and Y. L. Slominski, I. D. Radchenko, N. I. Efimenko, and A. I. Tolmachev, Ukr. Khim. Zh., 1980, 46, 61–63. The starting materials (E) are known, for example methyl 1-cyclohexene-1-carboxylate, or may be prepared from the known 1-cyclohexene carbonyl chloride.

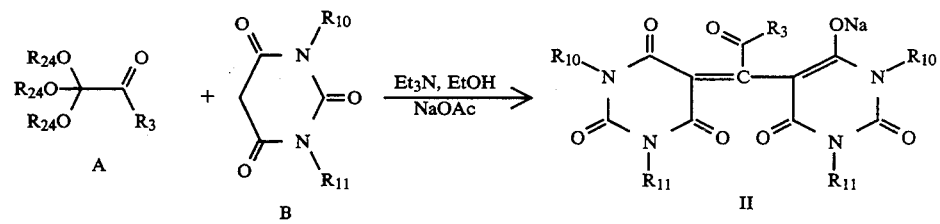
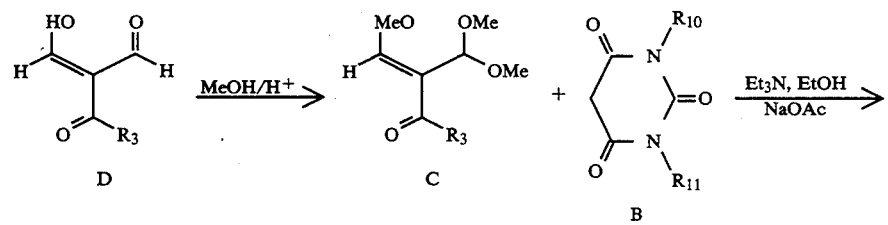
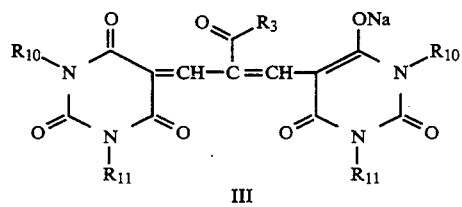
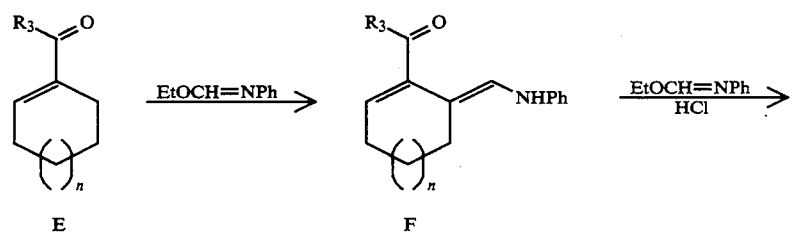
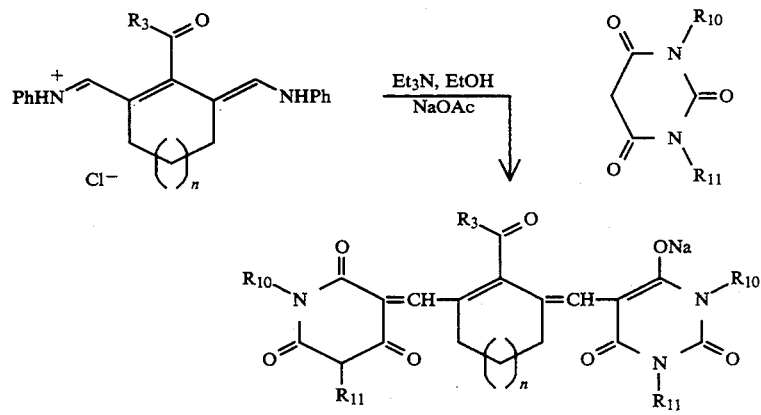
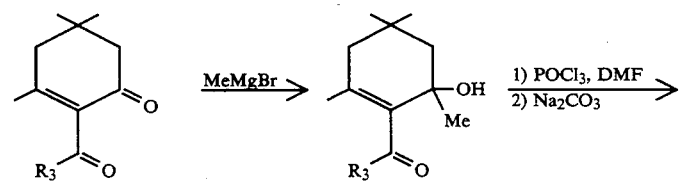

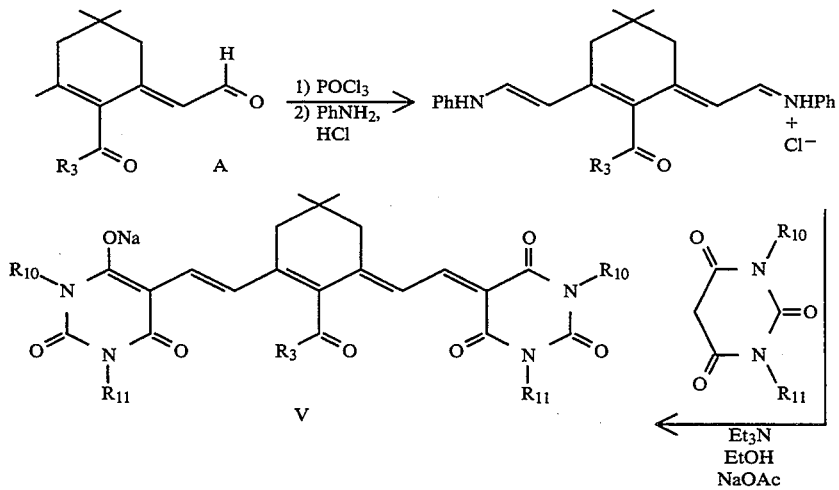

The pentamethine dyes of the present invention may be conveniently prepared by the reaction of an active methylene nucleus with a suitably substituted 2,4-dinitrophenylpyridinium salt, as already described above (see the reaction scheme used to prepare dyes of formula (If)). The dinitrophenylpyridinium salts used in reaction are prepared by the reaction of a suitably substituted pyridine with 2,4-dinitrochlorobenzene. Such reactions are routinely carried out in acetone, but we have found that butyronitrile is preferred when higher temperatures are required for the condensation reaction.

The photographic elements of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in Research Disclosure, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, with the reverse order on a reflective support being typical.

In the following discussion of suitable materials for use in elements of this invention, reference will be made to Research Disclosure, December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working, such as emulsions the grains of which are primarily surface-sensitive or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through IV. Color materials and development modifiers are described in Sections V and XXI. Vehicles which can be used in the elements of the present invention are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

With negative working silver halide a negative image can be formed. Optionally a positive (or reversal) image can be formed.

The photographic elements of the present may also use colored couplers (e.g. to adjust levels of interlayer correction) and masking couplers such as those described in EP 213.490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193,389; EP 301,477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. in *Photographic Science and Engineering*, Vol. 13, p. 1740 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. No. 4,346,165; 4,540,653 and 4,906,559); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in the elements of the invention are disclosed in Japanese Published Applications 83-09,959; 83-62,586; 90-072,629, 90-072,630; 90-072,632; 90-072,633; 90-072,634; 90-077,822; 90-078,229; 90-078,230; 90-079,336; 90-079,338; 90-079,690; 90-079,691; 90-080,487; 90-080,489; 90-080,490; 90-080,491; 90-080,492; 90-080,494; 90-085,928; 90-086,669; 90-086,670; 90-087,361; 90-087,362; 90-087,363; 90-087,364; 90-088,096; 90-088,097; 90-093,662; 90-093,663; 90-093,664; 90-093,665; 90-093,666; 90-093,668; 90-094,055; 90-094,056; 90-101,937; 90-103,409; 90-151,577.

Photographic elements of the present invention which include a dye of structure (I) herein, can include motion picture films. Motion picture film typically has a width of up to 100 millimeters (or only up to 70 or 50 millimeters), and a length of at least 30 meters (or optionally at least 100 or 200 meters).

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be ether polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where
ECD is the average equivalent circular diameter of the tabular grains in microns and
t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: *Research Disclosure*, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains to be used in the invention may be prepared according to methods known in the art, such as those described in *Research Disclosure I* and James, *The Theory of the Photographic Process*. These include methods such as ammoniacal emulsion making, neutral or acid emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements of the present invention, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30° to 80° C., as illustrated in *Research Disclosure*, June 1975, item 13452 and U.S. Pat. No. 3,772,031.

The silver halide may be sensitized by any sensitizing dyes and by any method known in the art, such as are described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in *Research Disclosure I*, section XVIII. This typically involves exposure to light in the visible region of the spectrum.

Photographic elements comprising the composition of the invention can be processed in any of a number of well-known photographic processes utilizing any of a number of well-known processing compositions, described, for example, in *Research Disclosure I*, or in James, *The Theory of the Photographic Process* 4th, 1977. For example, a negative image can be formed by processing the element with a suitable color developer followed by removal of silver and silver halide. In the case of processing a reversal color element, the element is typically first treated with a black and white developer followed by fogging of the silver halide (chemically or by light), followed by treatment with a color developer. Preferred color developing agents are p-phenylenediamines. Especially preferred are:

4-amino N,N-diethylaniline hydrochloride,
4-amino-3-methyl-N,N-diethylaniline hydrochloride,
4-amino-3-methyl-N-ethyl-N-($\beta$-(methanesulfonamido) ethylaniline sesquisulfate hydrate,
4-amino-3-methyl-N-ethyl-N-($\beta$-hydroxyethyl)aniline sulfate,
4-amino-3-$\beta$-(methanesulfonamido)ethyl-N,N-diethylaniline hydrochloride and
4-amino-N-ethyl-N-(2-methoxyethyl)-m-toluidine di-p-toluene sulfonic acid.

Development is followed by bleach-fixing, to remove silver or silver halide, washing and drying.

The invention is described further in the following examples.

Synthesis

A detailed description of the synthesis of representative intermediates and dyes of this invention is provided below.

Synthesis of 4-Carbamoyl-1-(2,4dinitrophenyl)-pyridinium chloride.

This material may be prepared by the procedure of H. Martin and E. Habicht, as described in British Patent 756, 271 (1956), (cf. C.A. 51: 9709h, 1957) or is preferably prepared by the following method.

To a solution of 85.1 grams (0.42 mol) of 1-chloro-2,4-dinitrobenzene in 400 mL of butyronitrile was added, with stirring, 48.85 grams (0.40 mol) isonicotinamide. The reaction mixture was stirred and heated to 112° C. in 45 minutes, held at 112° C. for 20 hours, then cooled to room temperature in 45 minutes. The precipitated product was collected by suction filtration and washed with butyronitrile, methanol, acetone and ether to afford after drying 115.8 grams (0.356 mol, 89.1% yield) of desired product, m.p.=252°–254° C. NMR and mass spectral data consistent with the assigned structure.

Elemental analysis: Theory: C=44.39, H=2.79, N=17.26; Found: C=44.23, H=2.87, N=17.17.

Synthesis of 4-Benzoyl-1-(2,4-dintirophenyl)pyridinium chloride.

To a solution of 85.1 grams (0.42 mol) of 1-chloro-2,4-dinitrobenzene in 100 mL of acetone was added, with stirring, 73.28 grams (0.40 mol) of 4-benzoylpyridine. The reaction mixture was stirred and heated to 50° C. in 45 minutes, held at 50° C. for 20 hours, then 200 mL of acetone was added and heating continued for another 2 hours. The product mixture was cooled to 40° C. and the precipitated product was collected by suction filtration. The crude product was slurried in 800 mL refluxing acetone for 30 minutes then collected by suction filtration from the warm slurry. Drying of the collected material gave 78.0 grams (0.202 mol, 50.5% yield) of desired product, m.p.=194°-195° C. NMR and mass spectral data consistent with the assigned structure. Elemental analysis: Theory: C=56.04, H=3.14, N=10.89; Found: C=55.70, H=3.20, N=10.95.

Synthesis of Dye 2.

Into a 100 mL round bottom flask was placed 6.8 grams (44 mmol) of 1,3-dimethylbarbituric acid, 30 mL of ethanol, and 6.0 grams (60 mmol) of triethylamine. The reaction was brought to 60° C. in an oil bath and 6.5 grams (20 mmol) of 4-carbamoyl-1-(2,4-dinitophenyl) pyridinium chloride was added all at once. The color of the reaction rapidly becomes deep blue. After 30 minutes heating a crystalline product precipitated. The product mixture was filtered while hot and the collected product washed with 20 mL ethanol and dried to give 11.8 grams of crude product. The crude product was slurried once in 100 mL of refluxing ethanol, collected, then treated with a solution of 4.47 grams (30 mmol) sodium iodide in 100 mL acetone. The slurry was heated to reflux, held at reflux for 20 minutes then filtered while hot. The resulting product was purified by successive slurries in hot ethanol and acetonitrile then dried to afford 3.8 grams (8.6 mmol, 43.2% yield) of the desired dye, m.p.=298°-302° C. (decomp.), absorbance maximum=615 nm (MeOH), extinction maximum=145,900. The NMR and mass spectral data were consistent with the structure of the product. HPLC analysis showed that the product was >98% pure. Elemental analysis: Theory: C=49.21, H=4.13, N=15.94; Found: C=46.29, H=4.28, N=15.33.

Synthesis of Dye 4.

Into a 100 mL round bottom flask was placed 11.08 grams (44 mmol) of 1,2-diphenylpyrazolidin-3,5-dione, 30 mL of ethanol, and 6.0 grams (60 mmol) of triethylamine. The reaction was brought to 60° C. in an oil bath and 6.5 grams (20 mmol) of 4-carbamoyl-1-(2,4dinitophenyl) pyridinium chloride was added all at once. The color of the reaction rapidly becomes deep blue and a crystalline product precipitated. The product mixture was filtered while hot and the collected product washed with 50 mL ethanol and dried to give 11.6 grams of crude product. The crude product was converted to the sodium salt by treatment with 4.5 grams (30 mmol) of sodium iodide dissolved in 100 mL methanol. The slurry was refluxed for one hour then cooled to 35° C. and the product collected by suction filtration. Washing with methanol and drying afforded 9.0 grams (14.2 mmol, 71.2% yield) of desired dye as a black powder, m.p.=268°-272° C., absorbance maximum=625 nm (MeOH), extinction maximum=201,500. The NMR and mass spectral data were consistent with the structure of the product. HPLC analysis showed that the product was >98% pure.

Synthesis of Dye 9.

A solution of 17.8 grams (44 mmol) of 3-acetyl-1-(2,5-disulfopenyl)-2-pyrazolin-5-one, disodium salt, in 50 mL of dry dimethylformamide was placed in a 100 mL round bottom flask and 4.4 grams (44 mmol) of triethylamine was added with stirring. The solution was heated to 60° C. over 10 minutes then 7.7 grams (20 mmol) of 4-benzoyl-1-(2,4-dintrophenyl)pyridinium chloride was added portionwise over a period of 2 minutes. The reaction mixture became very dark. After 45 minutes the warm reaction mixture was poured into 500 mL rapidly stirring acetone to precipitate the crude product. The crude product was collected by suction filtration then purified by successive slurrying in refluxing ethanol and methanol. The crude dye was dissolved in 25 mL water and 15 grams (0.1 mol) of sodium iodide was added. After stirring for 20 minutes the blue solution was poured into 250 mL methanol and then diluted with 100 mL ethanol. The resulting precipitated dye was collected and washed with ethanol and methanol to afford 3.4 grams (3.1 mmol, 15.6 % yield) of desired dye as the pentahydrate, m.p. >300° C., absorbance maximum=686 nm ($H_2O$), extinction maximum=104,000. The NMR and mass spectral data were consitent with the structure of the product. HPLC analysis showed that the product was >98% pure. Elemental analysis (pentahydrate salt): Theory: C=37.4, H=2.86, N=5.13, S=11.75; Found: C=34.54, H=2.39, N=4.59, S=11.07.

Synthesis of Dye 10.

Into a 100 mL round bottom flask was placed 6.8 grams (44 mmol) of 1,3-dimethylbarbituric acid, 30 mL of ethanol, and 6.0 grams (60 mmol) of triethylamine. The reaction was brought to 60° C. in an oil bath and 7.7 grams (20 mmol) of 4-benzoyl-1-(2,4-dinitophenyl) pyridinium chloride was added all at once. The color of the reaction rapidly becomes deep blue. After 30 minutes heating 30 mL of ethanol was added. The product slurry was stirred at 60° C. for 30 minutes more then the product mixture was filtered while hot and the collected product washed with 50 mL ethanol and dried to give 5.35 grams of crude product. The crude product was recrystallized from 200 mL of refluxing ethanol to afford 4.68 grams (8.1 mmol, 40.3% yield) of the desired dye, m.p.=230°-232° C. (decomp.), absorbance maximum=616 nm (MeOH), extinction maximum=158,000. The NMR and mass spectral data were consistent with the structure of the product. HPLC analysis showed that the product was >98% pure. Elemental analysis: Theory: C=62.16, H=6.4, N=12.08; Found: C=60.61, H=6.40, N=11.93.

The absorbance maximum in methanol of representative examples of the dyes described in this invention have been measured and are shown in Table 1 below.

TABLE 1

Methanol solution absorbance maxima of representative examples of acyl substituted pentamentine oxonol dyes.

| Dye No. | λ max  | Dye No. | λ Max  |
|---------|--------|---------|--------|
| 7       | 680 nm | 56      | 616 nm |
| 18      | 606 nm | 57      | 694 nm |
| 20      | 614 nm | 58      | 696 nm |
| 25      | 656 nm | 59      | 615 nm |
| 27      | 686 nm | 60      | 614 nm |
| 28      | 694 nm | 61      | 694 nm |
| 29      | 684 nm | 62      | 692 nm |

TABLE 1-continued

Methanol solution absorbance maxima of representative examples of acyl substituted pentamentine oxonol dyes.

| Dye No. | λ max | Dye No. | λ Max |
|---|---|---|---|
| 31 | 688 nm | 63 | 621 nm |
| 33 | 661 nm | 64 | 628 nm |
| 37 | 688 nm | 65 | 698 nm |
| 39 | 616 nm | 66 | 626 nm |
| 40 | 616 nm | 67 | 624 nm |
| 46 | 621 nm | 68 | 625 nm |
| 51 | 616 nm | 69 | 626 nm |
| 52 | 616 nm | 70 | 624 nm |
| 53 | 695 nm | 71 | 632 nm |
| 54 | 694 nm | | |
| 55 | 616 nm | | |

Photographic Testing

EXAMPLE 1

Photographic elements of the present invention were constructed in order to test the characteristics of such elements containing dyes of formula (I) versus elements containing the comparison dyes illustrated below.

Comparison Dyes:

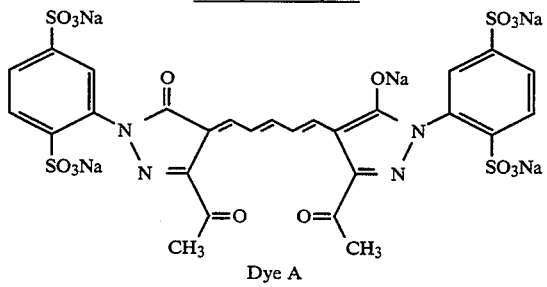

Dye A

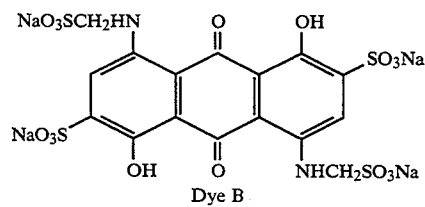

Dye B

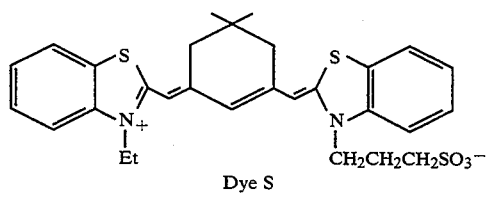

Dye S

Photographic elements were prepared and evaluated in accordance with the following procedure:

The dyes (Table I) were coated at a level of 0.0238 g/m² (2.2 mg/ft²), ±1%. Dyes were added to an aurous sulfide sensitized silver chloride emulsion (0.38 μm calculated cubic edge length), which had been spectrally sensitized with a red dye. Emulsion melts had the following coverages: silver at 0.184 g/m² (17 mg/ft²), gelatin 0.832 g/m² (77.0 mg/ft²).

The cyan coupler dispersion contained a cyan image forming coupler ((2-(alpha-(2,4-di-tert-amylphenoxy)-butyramido-4,6-dichloro-5-ethyl phenol)) at 0.424 g/m² (39.3 mg/ft²) and gelatin at 0.832 g/m²(77.0 mg/ft²). The coupler dispersion was added to the dye/silver chloride emulsion immediately before coating. The elements also included a gelatin overcoat (1.08 g/m²) and a gelatin undercoat layer (3.23 g/m²). The layers were hardened with bis (vinylsulfonyl)methyl ether at 1.7% of the total gelatin weight. Materials were coated on a resin-coated paper support.

To evaluate photographic sensitivity, the elements were exposed to a light source designed to simulate a color negative print exposure. The elements were then processed as follows: color development (45 sec, 35° C.), bleach-fix (45 sec, 35° C.), and stabilization or water wash (90 sec, 35° C.), followed by drying (60 sec, 60° C.). Speeds in Table I were obtained at a density of 1.0.

TABLE 1

| Sample | Dye | Laydown level | Red speed | Inherent speed |
|---|---|---|---|---|
| 1 | none | 0 | 161 | 146 |
| 2 | Comparative Dye A | 1× | 106 | 142 |
| 3 | Dye 54 | 1× | 80 | 138 |
| 4 | " | ⅔× | 95 | 140 |
| 5 | " | ⅓× | 120 | 143 |
| 6 | Dye 57 | 1× | 87 | 141 |
| 7 | " | ⅔× | 103 | 142 |
| 8 | " | ⅓× | 124 | 144 |
| 9 | Dye 58 | 1× | 86 | 141 |
| 10 | " | ⅔× | 100 | 144 |
| 11 | " | ⅓× | 123 | 144 |
| 12 | Dye 61 | 1× | 80 | 138 |
| 13 | " | ⅔× | 97 | 141 |
| 14 | " | ⅓× | 117 | 143 |
| 15 | Dye 62 | 1× | 85 | 140 |
| 16 | " | ⅔× | 100 | 142 |
| 17 | " | ⅓× | 121 | 144 |

Red Absorber dye laydown: 1× = 0.238 g/m² (±1%)

The above data demonstrates that the dyes of the invention provide much greater red speed reduction (therefore, they are better filter dyes) than the Comparison Dye A when coated at the same dye laydown (g/m²) and simultaneously do not adversely affect the inherant sensitivity of the emulsion spectrally sensitized with Sensitizing Dye S.

EXAMPLE 2

Photographic elements of the present invention were prepared accordance with the following format:

The dyes (Table 2) were coated at a level of 4.0 mg/ft² (0.0430 g/m²) to achieve speeds similar to that of Comparison Dye A based on extinction coefficient data. The dyes, evaluated in a cyan single layer coating format, were added to the protective overcoat layer. This layer also included poly(dimethyl siloxane) at 6.12 mg/ft² (0.0658 g/m²), poly(methyl methacrylate) beads at 0.468 mg/ft² (0.0050 g/m²), and gelatin at 90.8 mg/ft² (0.9773 g/m²).

The cyan coupler dispersion of the cyan layer contained: a cyan image forming coupler, compound 8 which is (2-(alpha-(3-pentadecylphenoxy)-butyramido4,6-dichloro-5-ethyl phenol), at 90.0 mg/ft² (0.9687 g/m²); oxidized developer scavenger, compound 4 which is (2,5-di-sec-dodecylhydroquinone), at 1.2 mg/ft² (0.0129 g/m²); and gelatin at 148.0 mg/ft² (1.5930 g/m²). The dispersion was added to sulfur and gold sensitized chloro-bromide emulsions immediately before coating. The two blended emulsions, known as components one and two, had cubic grain sizes of 0.15 μm and 0.24 μm, respectively. Emulsion melts consisted of component one silver at 36.9 mg/ft² (0.3971 g/m²), component two silver at 4.1 mg/ft² (0.0441 g/m²), and gelatin at 169.0 mg/ft² (1.8181 g/m²). Emulsions were spectrally sensitized with sensitizing Dye S, described above.

The layers were hardened with bis(vinylsulfonyl) methane at 1.75 % of the total gelatin weight. Materials were coated on a gelatin subbed acetate film support with a carbon based backing.

To evaluate photographic sensitivity, the elements were exposed for 1/500th of a second by means of a 3000° K. tungsten light source through a 0 to 3 neutral density step tablet, a heat absorbing filter, and filter designed to represent a motion picture color negative film.

The elements were then processed as follows: prebath (10 to 20 seconds), rinse, color development (3 minutes), stop bath (40 seconds), wash (40 seconds), first fixer (40 seconds), wash (40 seconds), ferrocyanide bleach (1 minute), wash (40 seconds), second fixer (40 seconds), wash (1 minute), and drying.

The elements were then read on a densitometer. The red speeds from those results appear in Table 2, and were obtained at a density of 1.0. In addition, Table 2 contains spectrophotometric measurements obtained on raw stock coatings which had been incubated for one week at −18° C./50% relative humidity ("check") and at 49° C./50 % relative humidity ("incubated"). The optical densities at lambda max ("$\lambda_{max}$") of the check and incubated coatings containing the dyes appear on Table 2.

TABLE 2

| Sample No. | Dye | Laydown | Red Speed | Optical Density at λmax Check | Incubated |
|---|---|---|---|---|---|
| 18 | Comp Dye A | 0.0756 | 117 | 0.753 | 0.738 |
| 19 | Comp Dye B | 0.111 | 96 | 0.278 | 0.285 |
| 20 | Dye 57 | 0.0430 | 101 | 0.503 | 0.482 |
| 21 | Dye 58 | 0.0430 | 102 | 0.444 | 0.437 |
| 22 | Dye 61 | 0.0430 | 104 | 0.442 | 0.441 |
| 23 | Dye 62 | 0.0430 | 109 | 0.427 | 0.426 |

Laydown in g/m².; Red Speed measured at 1.0 density on white light exposure Check coatings stored at −18° C. (0° F.), Incubated coating conditions: 49° C. (120° F.) at 50% R.H.

The date of Table 2 demonstrates that the dyes of the invention provide good red speed reduction at lower dye laydown than Comparison Dye A and Comparison Dye B in emulsions spectrally sensitized with Sensitizing Dye S and have good raw stock incubation stability.

EXAMPLE 3

Further photographic elements of the present invention were prepared and tested in the same manner as in Example 1 except that pairs of elements were prepared for each dye. One element of each pair was held for one hour at 40° C. while the other was held for 24 hours at 40° C. All melts were coated as part of the same coating event.

The results of the above are provided in Table 3 below ("OD change" means optical density change).

TABLE 3

| Sample Nos. | Dye | Laydown | Optical Density at λmax of coated melt 1 hr hold | 24 hr hold | OD change |
|---|---|---|---|---|---|
| 24 | Comp Dye A | 0.0238 g/m² | 0.864 | 0.824 | −0.040 |
| 25 | Dye 54 | 0.0238 | 0.802 | 0.785 | −0.017 |

TABLE 3-continued

| Sample Nos. | Dye | Laydown | Optical Density at λmax of coated melt 1 hr hold | 24 hr hold | OD change |
|---|---|---|---|---|---|
| 26 | Dye 57 | 0.0238 g/m² | 0.807 | 0.808 | +0.001 |
| 27 | Dye 58 | 0.0238 g/m² | 0.821 | 0.838 | +0.017 |

The data of Table 3 demonstrates that the dyes of the invention have excellent stability in gelatin melts which are held at 40° C. for 24 hours when compared to Comparison Dye A ("Comp Dye A").

EXAMPLE 4

Elements were constructed and tested according to the following:

Inventive Dye 58 and Comparison Dye A were added to a protective overcoat layer at levels of 7.0, 11.0, and 15.0 mg/ft2 (0.0753, 0.1184, and 0.1614 g/m2, respectively). In addition, this layer also contained poly (dimethyl siloxane) at 6.12 mg/ft2 (0.0658 g/m2), poly (methylmethacrylate) beads at 0.468 mg/ft2 (0.0050 g/m2), and gelatin at 90.8 mg/ft2 (0.9773 g/m2).

Dispersion and Emulsion formats were previously described in Example 2. An additional layer containing 400 mg/ft2 (4.3056 g/m2) gelatin was incorporated into the coating format between the dispersion/emulsion layer and the support. This gelatin pad was designed to simulate the combined thickness of an antihalation undercoat ("AHU") layer, yellow layer, and interlayer between the support and the cyan layer of a typical motion picture print film. This model was used to demonstrate the capacity of the dyes of elements of the invention to provide halation protection in the absence of rem jet. The layers were hardened with bis(vinylsulfonyl)methane at 1.5 % of the total gelatin weight. Materials were coated on polyethylene terephthalate with an antistatic layer on the backside of the support.

To evaluate halation latitude sensitivity, the elements were exposed for 32 seconds through the emulsion side by means of a 3200° K. tungsten light source with a 0.0 to 2.0 neutral density step tablet. The tablet is composed of two sections, the AIM and the HALATION LINE. The AIM is the area on the step chart that provides the characteristic D log E exposure. The HALATION LINE is a thin (4 mm), longitudinal line located in the center of the tablet; in this area of the element, direct exposure is completely eliminated, and only indirect exposure occurs.

The elements were then processed as follows: prebath (10 to 20 seconds), rinse, color development (3 minutes), stop bath (40 seconds), wash (40 seconds), first fixer (40 seconds), wash (40 seconds), accelerator (20 seconds), persulfate bleach (40 seconds), wash (40 seconds), second fixer (40 seconds), wash (1 minute), drying.

The elements were read on the emulsion side using two densitometry instruments. To obtain the characteristic D log E curve corresponding to normal exposure through the AIM section of the step tablet, the elements were read using a densitometer to locate the step that had a density of approximately 0.1 above D-min. This step and two steps above and below were densitometered. To obtain the halation D log E curve corresponding to the halation exposure, the areas on the elements in the HALATION LINE that were adjacent to the 5 AIM steps were read using a microdensitometer.

The halation curve was compared with the normally exposed curve by measuring the D log E separation of the two curves at a density of 0.10 above Dmin. The D log E separation data is summarized in Table 4.

TABLE 4

Halation Latitude Test Results

| Sample No. | Description | Separation difference Red Speed |
|---|---|---|
| 28 | Comp. A at 0.0753 g/m² | 1.19 |
| 29 | Comp. A at 0.118 g/m² | 1.46 |
| 30 | Comp. A at 0.161 g/m² | 1.81 |
| 31 | Inventive Dye 58 at 0.0753 g/m² | 1.35 |
| 32 | Inventive Dye 58 at 0.118 g/m² | 1.61 |
| 33 | Inventive Dye 58 at 0.161 g/m² | 1.84 |

"Comp. A" is comparison dye A.
Note: The larger the Separation Difference value, the greater the protection from halation effects.

The data of Table 4 demonstrates that the dyes of the invention provide better halation protection of a red spectrally sensitized silver halide emulsion than the Comparison Dye A, when both dyes are coated at the same level (mg/m²) of laydown.

Thus, it will be seen from the above description and examples that a new class of dyes has been discovered which are useful as photographic filter dyes. Useful photographic elements containing such dyes as filter dyes, have also been discovered. While the invention has been described in detail with particular reference to preferred embodiments, it will be understood that variations and modifications can be effected within the spirit and scope of the invention.

We claim:

1. A photographic element containing a silver halide emulsion layer and a dye of the structure (I) as a filter dye:

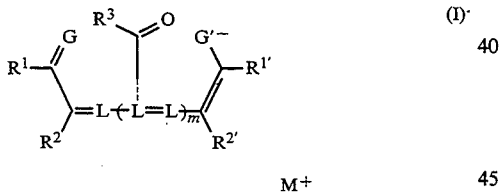

wherein:
G and G' are, independently, oxygen, substituted nitrogen, or C(CN)₂;
R¹, R¹', R², R²' independently represent H or a substituent, or R¹ and R², R¹' and R²' may form a ring;
R³ is an aryl, alkyloxy, aryloxy, amino, or heterocyclic, any of which may be substituted or unsubstituted;
m is 0, 1, 2 or 3;
all of the L together define a methine chain, each L representing a methine any of which may be substituted or unsubstituted;
the R³C(O)— is shown is substituted on the L at the middle of the methine chain; and
M⁺ is a cation.

2. An element according to claim 1 wherein R² and R²' represent a moiety in conjugation with the G⁻ and G'⁻, respectively.

3. An element according to claim 2 wherein R² and R²' each contains an atom with an available electron pair positioned in conjugation with G or G' which atom is an O, N, Se or S, or is a C with at least one electron withdrawing group bonded thereto, or either of R² or R²' is a group containing a benzene ring.

4. An element according to claim 2 wherein R¹ and R², and R¹' and R²', together with the carbon atoms to which they are attached and G or G', independently represent a benzoylacetonitrile, 2-pyrazolin-5-one, pyrazolindione, chromandione, cyclohexanedione, dioxanedione, furanone, isoxazolinone, pyrandione hydroxypyridone, pyrazolopyridine, tricyanopropene or barbituric acid, any of which may be substituted or unsubstituted.

5. A photographic element according to claim 2 wherein G and G' are, independently, O or —C(CN)₂.

6. A photographic element according to claim 2 wherein G and G' are both O.

7. A photographic element according to claim 2 wherein m is 2.

8. A photographic element containing a silver halide emulsion layer and a dye of the structure (Ia) as a filter dye:

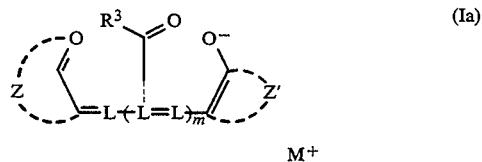

Z and Z' are atoms which, together with the C—CO to which they are attached, independently define a 2-pyrazolin-5-one, pyrazolindione or barbituric acid, any of which may be substituted or unsubstituted;
R³ is an aryl, alkyloxy, aryloxy, amino, or heterocyclic, any of which may be substituted or unsubstituted;
m is 0, 1, 2 or 3;
all of the L together define a methine chain, each L representing a methine any of which may be substituted or unsubstituted;
the R³C(O)— shown is substituted on the L at the middle of the methine chain; and
M⁺ is a cation.

9. A photographic element containing a silver halide emulsion layer and a dye of the structure (Ib) as a filter dye:

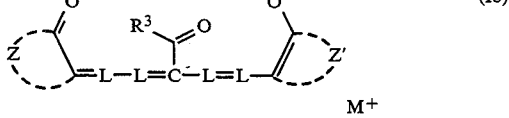

Z and Z' are atoms which, together with the C—CO to which they are attached, independently define a 2-pyrazolin-5-one, pyrazolindione or barbituric acid, any of which may be substituted or unsubstituted;
R³ is an alkyl, aryl, alkyloxy, aryloxy, amino, or heterocyclic, any of which may be substituted or unsubstituted;
m is 0, 1, 2 or 3;
all of the L together define a methine chain, each L representing a methine any of which may be substituted or unsubstituted; and
M⁺ is a cation.

10. A photographic element according to claim 8 wherein the dye is of formulae (Ic), (Id) or (Ie):

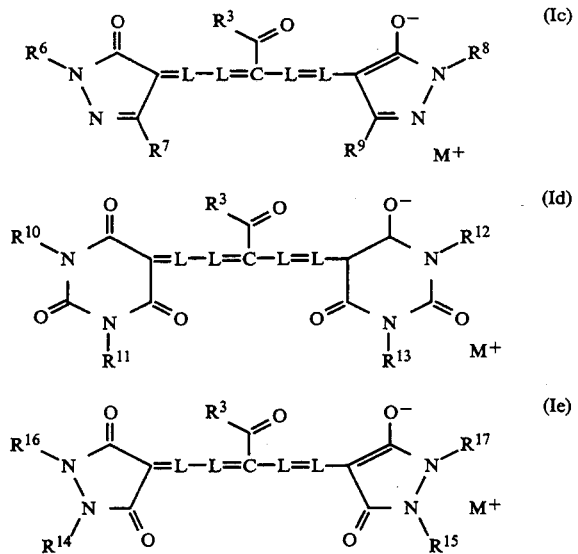

R7 and R9 are independently H, or alkyl, alkoxy, aryl, aryloxy, acyl, amino, cyano, carbonamido or carbamoyl, any of which may be substituted or unsubstituted; and R6, R8, R10, R11, R12, R13, R14, R15, R16 and R17 are independently H, alkyl or aryl, any of which may be substituted or unsubstituted.

11. A photographic element according to claim 2 wherein the dye has at least one acid or acid salt substituent.

12. A photographic element according to claim 2 wherein the dye has at least one carboxy, sulfonamido, sulfamoyl, sulfato or sulfo substituent.

13. A photographic element according to claim 2 wherein the element additionally comprises a support and radiation sensitive silver halide emulsion layer, and wherein the dye is a filter dye which is in a hydrophilic layer different from said radiation-sensitive layer, said hydrophilic layer being located on the same side of the support as said radiation sensitive layer.

14. A photographic element according to claim 2 wherein the element additionally comprises a support and radiation sensitive silver halide emulsion layer, and wherein the dye is a filter dye which is in a hydrophilic layer different from said radiation-sensitive layer, said hydrophilic layer being located on the side of the support opposite to said radiation sensitive layer.

15. A photographic element according to claim 2 wherein the dye is in the form of a dispersion of solid particles.

16. A photographic element according to claim 2 wherein the element additionally comprises a radiation sensitive silver halide emulsion layer, and wherein the dye is a sensitizing dye adsorbed to the silver halide.

17. A photographic element according to claim 13 wherein said filter dye is dissolved in said hydrophilic layer.

18. A photographic element according to claim 15 wherein said dye particles have a mean diameter of 0.01 to 100 micrometers.

19. A photographic element according to claim 2 wherein said dye is present in an amount in the range of 0.1 to 1000 mg/m².

20. A photographic element according to claim 1 wherein the element is a motion picture film.

21. A photographic element according to claim 2 wherein the element is a motion picture film.

22. A photographic element according to claim 9 wherein R³ is aryl, alkyloxy, aryloxy, amino, or heterocyclic, any of which may be substituted or unsubstituted.

23. A photographic element according to claim 1 wherein R³ is aryl, amino, or heterocyclic, any of which may be substituted or unsubstituted.

24. A photographic element according to claim 10 wherein R³ is aryl, amino, or heterocyclic, any of which may be substituted or unsubstituted.

25. A photographic element according to claim 1 wherein R³ is amino, which may be substituted or unsubstituted.

* * * * *

IN THE UNITED STATES PATENT AND TRADEMARK OFFICE
CERTIFICATE OF CORRECTION

PATENT NO. : 5,451,494

DATED : September 19, 1995

INVENTOR(S) : Donald R. Diehl et al.

It is certified that errors appear in the above-identified patent and that said Letters Patent is hereby corrected as shown below:

Column 43, line 59, remove the first ocurrence of "is"

Column 43, line 65, "$R^2$and" should read --$R^2$ and--

Column 43, line 66, "$R^2$each" should read --$R^2$ each--

Column 43, line 67, "G'which" should read --G' which--

Column 44, line 25, should read

Column 46, lines 37-39, delete Claim 24

Column 46, line 40, "25." should read --24.--

Signed and Sealed this

Twelfth Day of December, 1995

Attest:

Attesting Officer

BRUCE LEHMAN
Commissioner of Patents and Trademarks